(12) United States Patent
Amster et al.

(10) Patent No.: US 7,951,602 B2
(45) Date of Patent: May 31, 2011

(54) MASS DEFECT LABELING AND METHODS OF USE THEREOF

(75) Inventors: I. Jonathan Amster, Athens, GA (US); Robert S. Phillips, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 543 days.

(21) Appl. No.: 11/845,856

(22) Filed: Aug. 28, 2007

(65) Prior Publication Data

US 2009/0061523 A1 Mar. 5, 2009

Related U.S. Application Data

(60) Provisional application No. 60/840,559, filed on Aug. 28, 2006.

(51) Int. Cl.
*G01N 33/48* (2006.01)
(52) U.S. Cl. ............ 436/86; 436/89; 436/173; 564/218; 568/56
(58) Field of Classification Search .................... 436/86, 436/89, 173; 564/218; 568/56
See application file for complete search history.

(56) References Cited

U.S. PATENT DOCUMENTS

2006/0263886 A1* 11/2006 Peters et al. ................... 436/56

OTHER PUBLICATIONS

Hernandez, Hilda et al. "Mass defect labeling of cysteine for improving peptide assignment in shotgun proteomic analyses." Anal. Chem. (Apr. 2006) 78 p. 3417-3423.*

Li, Chunyan et al. "A matrix-assisted laser desorption/ionization compatible reagent for tagging tryptophan residues." Eur. J. Mass Spectrom. (Sep. 2006) 12 p. 213-221.*

Kuyama, Hiroki et al. "An approach to quantitative proteome analysis by labeling tryptophan residues." Rapid Comm. Mass Spectrom. (2003) 17 p. 1642-1650.*

Strohalm, Martin et al. "Tryptophan modification by 2-hydrooxy-5-nitrobenzyl bromide studied by MALDI-TOF mass spectrometry." (2003) 312 p. 811-816.*

Leitner, Alexander et al. "Current chemical tagging for proteome analysis by mass spectrometry." J. Chromatography (2004) 813 p. 1-26.*

Luftmann, Heinrich et al. "MALDI-TOF mass spectrometry for detecting impurities in ester-end-functionalized poly(tetrahydrofuran), poly(propylene glycol), and poly(caprolactone) telechelics." Macromolec. (2003) 36 p. 6316-6324.*

Garratt, Dennis G. et al. "Electrophilic additions to allenes. VI. The role of steric versus electronic effects in the reactions of arenesulphenyl halides with allenes." Can. J. Chem. (1980) 58 p. 2737-2744.*

(Continued)

*Primary Examiner* — Yelena G Gakh
*Assistant Examiner* — Christopher A Hixson
(74) *Attorney, Agent, or Firm* — Thomas, Kayden, Horstemeyer & Risley, LLP

(57) ABSTRACT

Mass defect labeled peptides and methods of identifying peptides are provided. In particular, embodiments of the present disclosure include mass defect labels for polypeptides that include at least one cysteine and/or at least one tryptophan and methods of using the mass defect labels to identify polypeptides. One embodiment, among others, includes a mass defect labeled peptide including at least one cysteine residue labeled with 2,4-dibromo-acetanilide. Another embodiment, among others, includes a mass defect labeled peptide including at least one tryptophan residue labeled with 4,6-dibromo-2-trifluoromethylphenylsulfenyl chloride.

8 Claims, 12 Drawing Sheets

OTHER PUBLICATIONS

Link, Helmut von. "Synthese von 2,4-diamino-thieno[2,3-d]pyrimidin-derivaten." Helv. Chem. Acta (1990) 73 p. 797-803.*

Pasquarello, Carla et al. "N-t-butyliodoacetamide and iodoacetanilide: two new cysteine alkylating reagents for relative quantitation of proteins." Rapid Communications in Mass Spectrometry (2004) 18 117-127.*

Ricks, Allen et al. "Mass defect labeling for enhanced protein identification." Abstracts of Papers, 229th ACS National Meeting, San Diego, CA, Mar. 13-17, 2005. CHED-335.*

Kujawinski, Elizabeth B. et al. "High-resolution Fourier transformation ion cyclotron resonance mass spectrometry of humic and fulvic acids: Improvements and comparisons." Analytical Chemistry (2002) 74 413-419.*

* cited by examiner

Tryptophan     Tag $R_1 = NO_2$, $R_2 = H$ (2-NPSCl)
$R_1 = CF_3$, $R_2 = H$ (2-TFPSCl)
$R_1 = CF_3$, $R_2 = Br$ (MDL)

Protein (A) UNLABELED BOMBESIN;   (B) LABELED BOMBESIN;

(A) UNLABELED MYOGLOBIN DIGEST;   (B) LABELED MYOGLOBIN DIGEST;

MASS DEFECT LABELING AND METHODS OF USE THEREOF

CROSS-REFERENCE TO RELATED APPLICATION

This application claims priority to U.S. provisional applications entitled, "MASS DEFECT LABEL FOR CYSTEINE AND METHODS OF USE THEREOF," having Ser. No. 60/840,559, filed on Aug. 28, 2006, which is entirely incorporated herein by reference.

STATEMENT REGARDING FEDERALLY SPONSORED RESEARCH OR DEVELOPMENT

This invention was made with government support under agreement RR019767 awarded by the National Institutes of Health. The Government has certains rights in the invention.

BACKGROUND

The primary goal of a proteomic analysis is to be able to systematically identify and quantify the majority of proteins expressed in a cell or tissue. The conventional approach for conducting proteome-wide studies is two-dimensional polyacrylamide gel electrophoresis (2D-PAGE), where a large number of proteins can be separated on the basis of their isoelectric point and molecular weight. Although 2D-PAGE technology has been the chief technology for proteomic analysis to date, it has recognized limitations, such as a bias toward the most abundant proteins and dynamic range and protein solubility issues that complicate the detection and separation of low-abundance and hydrophobic proteins. In recent years, a number of researchers have focused on improving proteomic analyses via the development of shotgun proteomic methods. These methods identify and quantify proteins that have not been separated prior to digestion. The basis of this approach is to perform a batch digestion of an unseparated protein mixture, to separate the resulting peptides by one or more dimensions of liquid chromatography, and to identify the proteins from which the peptides derive by mass spectrometry analysis.

Two mass spectrometry approaches for shotgun proteomic analysis have been reported. First is the use of tandem mass spectrometry to generate fragmentation data that can be used by search engines to identify the protein origin of the peptides. These methods are able to detect and identify a wide variety of protein classes including those with extremes in isoelectric point, molecular weight, abundance, and hydrophobicity. However, these methods are time consuming and produce very large data sets, as they require the generation of a fragmentation spectrum for each peptide in a mixture that contains thousands of components. A second approach is the use of accurate mass measurement to identify proteins. If the molecular masses of the peptides from a batch digest are measured with high enough mass measurement accuracy (MMA), a reasonable fraction of their masses can uniquely identify them by comparison to a list of masses for all of the possible proteolytic peptides predicted from an in silico digest of the genome. Other experimental information can be used to increase the fraction of identified peptides, for example, HPLC retention time. Methods that combine MMA with the MS/MS capabilities have also been reported.

Thus, there is a need in the industry to overcome these deficiencies.

SUMMARY

Briefly described, embodiments of this disclosure include mass defect labeled peptides, methods of identifying peptides, and the like. One exemplary peptide, among others, includes: a mass defect labeled peptide including at least one cysteine, wherein at least one of the cysteine residues are labeled with 2,4-dibromo-acetanilide.

One exemplary method of identifying peptides, among others, includes: labeling at least one cysteine in a target peptide with a mass defect label, wherein the mass defect label is 2,4-dibromo-acetanilide; introducing the target peptide to a mass spectrometry system; and obtaining a mass spectrum of the target peptide.

One exemplary peptide, among others, includes: a mass defect labeled peptide including at least one tryptophan, wherein at least one of the tryptophan residues are labeled with 4,6-dibromo-2-trifluoromethylphenylsulfenyl chloride.

One exemplary method of identifying peptides, among others, includes: labeling at least one tryptophan in a target peptide with a mass defect label, wherein the mass defect label is 4,6-dibromo-2-trifluoromethylphenylsulfenyl chloride; introducing the target peptide to a mass spectrometry system; and obtaining a mass spectrum of the target peptide.

BRIEF DESCRIPTION OF THE DRAWINGS

The components in the drawings are not necessarily to scale. Moreover, in the drawings, like reference numerals designate corresponding parts throughout the several views.

FIG. 4(A) illustrates the calculated isotopic pattern for the peptide MPCTEDYLSLILNR SEQ ID NO: 1 from bovine serum albumin (residues 445-458) without the dibromoacetanilide mass defect label, while FIG. 4(B) illustrates the calculated isotopic pattern with the dibromoacetanilide mass defect label.

FIG. 8(A) illustrates a histogram of monoisotopic masses for all the possible peptides from in-silico tryptic digestion of *Methanococcus maripaludis* over the range 1500-1501 Da before mass defect labeling, while FIG. 8(B) illustrates a histogram of monoisotopic masses for all the possible peptides after mass defect labeling.

DETAILED DESCRIPTION

Figure 1:
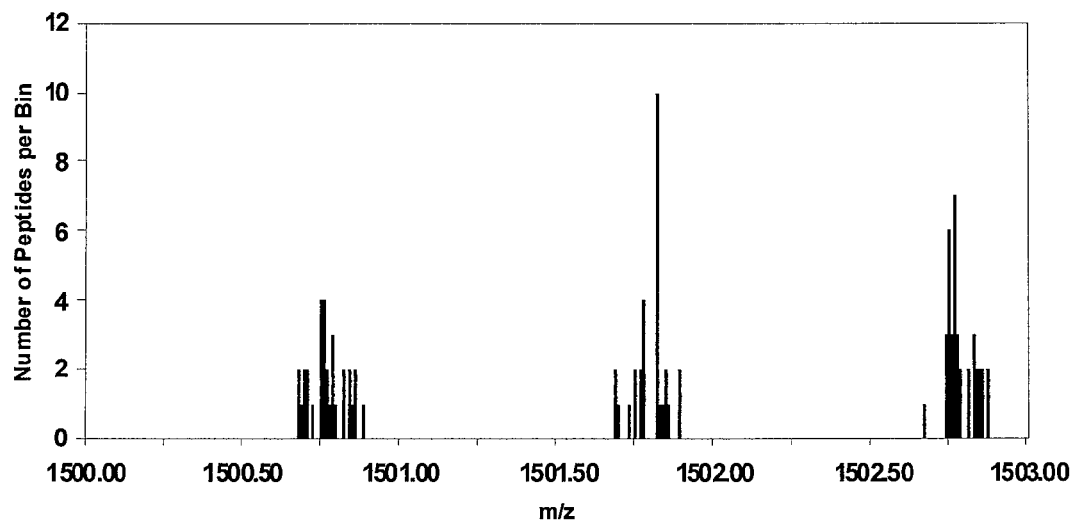
FIG. 1 illustrates a histogram of the molecular weight distribution of the predicted tryptic peptides of M. maripaludis over the range 1500-1503 Daltons (Da), which illustrates the distribution of mass defects of peptides. The bin size is 0.01 atomic mass units (amu). Peptide masses are observed to cluster in approximately one-third of the available mass space.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible.

Embodiments of the present disclosure will employ, unless otherwise indicated, techniques of chemistry, inorganic chemistry, mass spectrometry, physics, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "mass defect" refers to the difference between the exact monoisotopic mass of a compound and its nominal molecular weight, that is the weight based on the nucleon values of the most abundant isotope of each element (e.g., 12 amu for C, 16 amu for 0, etc).

Discussion

Mass defect labeled peptides and methods of identifying peptides are provided. In particular, embodiments of the present disclosure include mass defect labels for polypeptides that include at least one cysteine and/or at least one tryptophan and methods of using the mass defect labels to identify polypeptides. Additional details about embodiments of the present disclosure are described in Examples 1 and 2.

In general, there is a narrow distribution of mass defects in unlabeled polypeptides. The narrow distribution of mass defects that is characteristic of peptides arises in part from the small mass defect of their component elements, and from the uniform stoichiometry of peptides. The peptide masses tend to occupy only one-third of the available mass scale, which causes some of the predicted masses to overlap, even at a mass tolerance of 10 ppm. To shift some of the peptide masses to the region of the mass scale that is unpopulated, the mass defects of a portion of the peptides can be performed by derivatizing one or more amino acids (e.g., cysteine and/or tryptophan) with a reagent (e.g., 2,4-dibromo-(2'iodo)acetanilide (cysteine) and 4,6-dibromo-2-trifluoromethylphenylsulfenyl chloride (tryptophan)) that introduces a large mass defect. This is accomplished by introducing a heavy element (e.g., bromine) with a large mass defect into the elemental composition.

Embodiments of the present disclosure can include one or more of the following features or advantages. First, embodiments of the present disclosure enable both unlabeled peptides and mass defect labeled peptides to be analyzed simultaneously, which eliminates the need for separation prior to analysis and allows the detection of peptides that do not contain cysteine and/or tryptophan. Second, embodiments of the present disclosure enable improved analysis of complex polypeptide mixtures because the mass defect labeled peptides reduce congestion in a mass spectrum. In other words, the mass spectrum is de-convoluted because regions of the mass space that were previously unoccupied will be populated by the mass defect labeled peptides. Third, embodiments of the present disclosure enable improved analysis of complex polypeptide mixtures because the mass defect labeling methods improve the detectability and identification specificity of previously missed polypeptides. Fourth, embodiments of the present disclosure can be conducted using matrix assisted laser desorption ionization Fourier transform mass spectrometry (MALDI-FTMS) without requiring the use of tandem MS, which demands the acquisition of much larger data sets, and requires significantly more computational analysis of the data.

Figure 3:
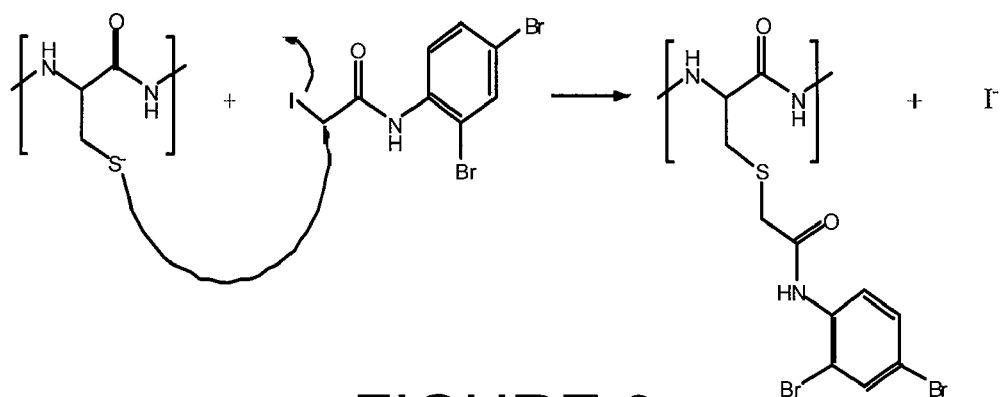
FIG. 3 illustrates the mechanism of an alkylation reaction of a cysteine-containing peptide with 2,4-dibromo-(2'-iodo) acetanilide.

In an embodiment, the mass defect label is a derivative of iodoacetamide (e.g., 2,4-dibromo-(2'iodo)acetanilide) that reacts specifically with cysteine. The mechanism of this reaction and the mass defect labeled polypeptide are shown in FIG. 3 of Example 1. The mass defect labeled polypeptide should be about 0.3 amu (or a factor thereof for multiple labeling) below the unlabeled polypeptide. In addition, since cysteine is not found in as high abundance in tryptic peptides, there is less probability of mass overlap.

A target polypeptide or plurality of target polypeptides can be labeled by mixing the iodoacetamide compound with the target polypeptide (before or after digestion). Once the target polypeptide is labeled, the labeled polypeptide is analyzed using a high-resolution mass spectrometry system (e.g., MALDI-FTICR and the like). The labeled target polypeptides will be offset by an amount consistent with the number of labeled cysteines. As a result, the identification of polypeptides can be improved during proteome analysis (e.g., shotgun proteome analysis).

In an embodiment, a polypeptide mixture can be analyzed using embodiments of the present disclosure. The polypeptide mixture can be labeled using the iodoacetamide mass defect label. Then the entire polypeptide mixture can be analyzed. The labeled polypeptides will be offset by an amount consistent with the number of labeled cysteines. Because the peptides masses are shifted to a range of values where masses do not occur normally, there is less overlap of predicted masses, and thus the identification of polypeptides by accurate mass measurement can be improved during proteome analysis (e.g., shotgun proteome analysis).

Figure 9:
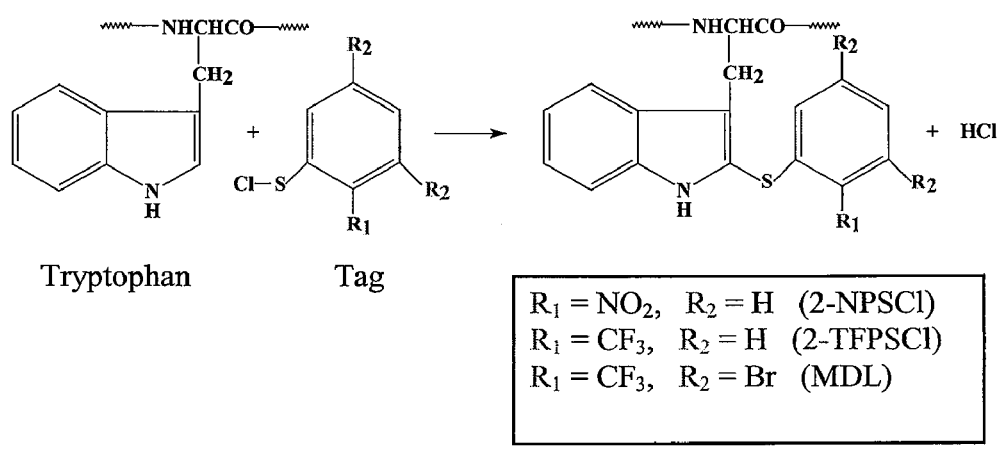
FIG. 9 illustrates a mass defect label that has specific reactivity to tryptophan.
Figure 9:
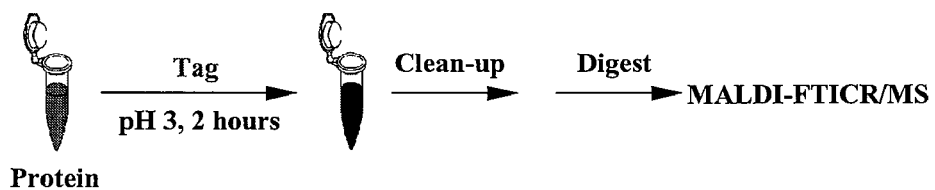

In another embodiment, the mass defect label is a derivative of 2-trifluoromethylphenylsulfenyl chloride (e.g., 4,6-dibromo-2-trifluoromethylphenylsulfenyl chloride) that reacts specifically with tryptophan. The mechanism of this reaction and the mass defect labeled polypeptide are shown in FIG. 9 of Example 2. The mass defect labeled polypeptide should be about 0.2-0.6 amu (or a factor thereof for multiple labeling) below the unlabeled polypeptide.

A target polypeptide or plurality of target polypeptides can be labeled by mixing the derivative of 2-trifluoromethylphenylsulfenyl chloride compound with the target polypeptide (before or after digestion). Once the target polypeptide is labeled, the labeled polypeptide is analyzed using a high-resolution mass spectrometry system (e.g., MALDI-FTICR and the like). The labeled target polypeptides will be offset by an amount consistent with the number of labeled tryptophans. As a result, the identification of polypeptides can be improved during proteome analysis (e.g., shotgun proteome analysis).

In an embodiment, a polypeptide mixture can be analyzed using embodiments of the present disclosure. The polypeptide mixture can be labeled using the derivative of 2-trifluoromethylphenylsulfenyl chloride compound mass defect label. Then the entire polypeptide mixture can be analyzed. The labeled polypeptides will be offset by an amount consistent with the number of labeled tryptophans. As a result, the identification of polypeptides can be improved during proteome analysis (e.g., shotgun proteome analysis).

Embodiments of the present disclosure include labeling at least one cysteine and at least one tryptophan on a polypeptide. In particular, the polypeptide can be labeled with both 2,4-dibromo-(2'iodo)acetanilide (cysteine) and 4,6-dibromo-2-trifluoromethylphenylsulfenyl chloride (tryptophan).

In another embodiment, a polypeptide mixture can labeled with a combination of mass defect labels (e.g., 2,4-dibromo-(2'iodo)acetanilide (cysteine) and 4,6-dibromo-2-trifluoromethylphenylsulfenyl chloride (tryptophan)), where some polypeptides will be labeled with both mass defect labels, where some polypeptides will be labeled with only of the one of the two defect labels, and where some polypeptides will not be labeled with either mass defect label.

The mass defect labeled polypeptides or mixtures including mass defect labeled polypeptides and unlabeled polypeptides can be analyzed using mass spectrometry systems. The mass spectrometry system can include systems such as, but not limited to, ion trap mass analyzer systems (IT-MS), ion cyclotron resonance mass analyzer system (ICR-MS) (e.g., FTICR-MS), and orbitrap systems, as well as with other ion trapping systems. The mass spectrometry system source can include sources such as, but not limited to, electrospray ionization sources, atmospheric pressure chemical ionization sources, inductively coupled plasma ion sources, glow discharge ion sources, electron impact ion sources, laser desorption/ionization ion sources, radioactive sources, as well as other ion sources compatible with the mass spectrometry systems mentioned above. In an embodiment the mass spectrometry system is a MALDI-FTMS and, in particular, a MALDI-FTICR.

EXAMPLES

Now having described the embodiments of the present disclosure, in general, Examples 1 and 2 describe some additional embodiments of the present disclosure. While embodiments of the present disclosure are described in connection with Examples 1 and 2 and the corresponding text and figures, there is no intent to limit embodiments of the present disclosure to these descriptions. On the contrary, the intent is to cover all alternatives, modifications, and equivalents included within the spirit and scope of embodiments of the present disclosure. Additional detail regarding Example 1 are described in Anal. Chem. 2006, 78, 3417-3423, which is incorporated herein by reference.

Example 1

In this Example, we describe a new method for improving the specificity of protein identification by accurate mass measurement of peptides. The improvement is based upon the derivatization of a specific amino acid with a reagent that changes the mass defect of the peptide. For the purpose of discussion, we refer to the mass defect as the difference between the exact monoisotopic mass of a compound and its nominal molecular weight, that is the weight based on the nucleon values of the most abundant isotope of each element (e.g., 12 amu for C, 16 amu for O, etc). Peptides are composed principally of elements from the first two rows of the periodic table. These elements have mass defects that lie in the range of +/−0.008 amu. The mass defect of peptide molecules is approximately +0.05 amu per 100 amu of molecular weight, i.e. a 1 kDa peptide has a mass defect of approximately +0.5 amu, and a 2 kDa peptide has a mass defect of 1 amu. The positive mass defect is a result of the high stoichiometric proportion of hydrogen atoms in a peptide molecular formula (the hydrogen mass defect is +0.0078 amu). Although peptide molecules have significant mass defects because of the large number of atoms from which they are assembled, the distribution of mass defects is generally narrow, causing peptide molecular weights at any given nominal mass to occupy only a small portion of a unit mass. This is illustrated in FIG. 1, which shows a histogram of monoisotopic masses for the 125 possible tryptic peptides (up to 1 missed cleavage) with molecular weights between 1500 and 1503 that one predicts for all proteins in the sequence database for the organism *Methanococcus maripaludis*. This organism has 1722 open reading frames, which is about average for a single cell organism, and has approximately 95,700 predicted tryptic peptides above with molecular weights 700 amu (allowing up to 1 missed cleavage), and the predicted peptide mass distribution is similar to that of any organism. Because of the narrow distribution of mass defects for peptides, their molecular weights cluster into one-third of the total mass space causing masses to overlap, and reducing the specificity of a peptide mass for identifying the protein origin. Greater specificity would be possible if the peptide masses were distributed more evenly across the mass scale.

The narrow distribution of mass defects for a compound class has been noted previously by other researchers in mass spectrometry. Perfluoroalkanes have distinctly different mass defects that do not overlap those of most other organic compounds, and have long been employed as internal calibrants for exact mass measurements. The components of complex mixtures of small molecules can be assigned a Kendrick mass defect value, which allows homologous series to be assigned to various compound classes. Labeling the N-terminus of a protein with a compound that alters the mass defect is used to distinguish the N-terminal peptide fragments from C-terminal and internal fragments produced by nozzle-skimmer dissociation of intact proteins, and is the basis of a commercial reagent (IDBEST™) and process. We report here a method for altering the mass defects of a selected fraction of the peptides in a batch digest of a proteome so that the resulting peptides can be more readily identified by accurate mass measurement.

Experimental Section

Reagent Synthesis: The cysteine-alkylating reagent, 2,4-dibromo-(2'-iodo) acetanilide, was prepared by addition of 5.4 mmol (0.46 mL) of oxalyl chloride (Acros Organics, Morris Plains, N.J.) in 2.7 mL of dry dichloromethane to 1 equivalent (1 g) of 2-iodoacetic acid (Acros Organics) in 4 mL of dry dichloromethane. This mixture was stirred for 3 h at 0° C. under nitrogen to yield a pink solution (2-iodoacetylchloride). This solution was added dropwise with stirring to 1 equivalent (1.3 g) of 2,4-dibromoaniline (Acros Organics) in 10 mL of dry dichloromethane. A white crude solid appeared as a precipitate, and was collected by filtration and purified by recrystallization from hot water to give the final product in 70% yield. The structure of the purified 2,4-dibromo-(2'-iodo) acetanilide was confirmed by $^1$H-NMR and mass spectrometry (NMR and MS spectra are included as supplementary data.) All reagents and solvents were used as purchased without further purification.

Protein Labeling: The labeling of cysteine before versus after tryptic digestion was compared for a number of proteins. We consistently find that the best results are obtained by labeling before digestion, as it is easier to remove the excess labeling reagent from a protein solution than from a solution of lower molecular weight peptides. Each protein standard was dissolved in alkaline solution (10 mM ammonium bicarbonate) to make a 1 mg/mL solution, and denatured by heating at 95° C. Disulfide bonds were reduced by addition of tris (2-carboxyethyl)phosphine (Pierce Biotechnology, Rockford, Ill.). The protein then underwent reaction with a 100 fold molar excess of 2,4-dibromo-(2'-iodo) acetanilide at pH 8 for 90 minutes in the dark at room temperature. Prior to trypsin digestion, the derivatized protein was subjected to centrifugal size exclusion chromatography using a 3 mL spin column packed with Sephadex G-25 (Aldrich, St. Louis, Mo.) to remove excess 2,4-dibromo-(2'-iodo) acetanilide. Trypsin digestion was performed under standard conditions (Promega, Madison Wis.), i.e. at 37° C., pH 7, for 18 hours.

Proteome Labeling: Whole cell lysates were extracted from *Methanococcus maripaludis* that was grown on minimal media with ammonium sulfate as the sole source of nitrogen. Cells were grown using ammonium sulfate both with the naturally occurring isotopic composition (99.6% $^{14}$N, 0.4% $^{15}$N) and with 98% $^{15}$N-enrichment. The cells were concentrated by centrifugation at 10000 rpm for 30 minutes; lysis of the cells was performed with a French press. DNA was digested and removed from the extract by adding DNAase to the sample followed by centrifugation. Equal amounts of protein extracts were mixed together before batch trypsinolysis. Prior to denaturing and labeling of the proteome, small molecules were removed by centrifugal size exclusion spin columns packed with Sephadex G-25. Subsequent treatment of the sample followed the procedure described above for labeling of the protein standards. Total protein concentrations were determined spectrophotometrically measuring at 562 nm using a bicinchoninic acid protein assay kit (Pierce, Rockford, Ill.).

Mass Spectrometry: Samples were analyzed by matrix assisted laser desorption/ionization (MALDI) Fourier transform ion cyclotron resonance (FTICR) mass spectrometry using a 7 Tesla magnet (Bruker Daltonics Inc, Billerica, Mass.). This instrument is equipped with a SCOUT 100 MALDI source which desorbs ions at elevated pressure (~1 mTorr) to suppress metastable decomposition. Conditions for operation of the FTICR MS were similar to those reported previously, and external mass calibration was established using a peptide mixture generated by tryptic digestion of chicken egg albumin (Sigma, St. Louis, Mo.). The MALDI matrix was 2,5-dihydroxybenzoic acid (DHB) (Lancaster, Pelham, N.H.).

High Performance Liquid Chromatography: Separations of peptide mixtures were performed on an UltiMate™ Plus, FAMOS™ by Dionex (Sunnyvale, Calif.). Reverse-phase columns used were: 1) 75 μm i.d.×15 cm, C18 PepMap100, 3 μm, 100 Å; and 2) 75 μm i.d.×15 cm, C8 PepMap100, 3 μm, 100 Å (LC Packings-Dionex). Mobile phase A was water/acetonitrile/trifluoroacetic acid (98:2:0.1 by volume), and mobile phase B was acetonitrile. A gradient from 0-100% B over 90 min was used at an approximate column flow of 300 mL/min; the total run time was 120 minutes. The eluate was collected onto a stainless steel MALDI target at 60 second intervals using a Probot™ Micro Fraction Collector (LC Packings-Dionex). The MALDI matrix was added after the fraction collection was completed, requiring resuspension of the dried, fractionated peptides in 0.5 μL of the matrix solution (1 M DHB in 50:50:0.1 water:acetonitrile:trifluoroacetic acid.)

Protein Identification: The molecular weight of the peptides and their nitrogen stoichiometry were determined from the MALDI-FTICR mass spectrum. The number of nitrogen atoms in each peptide was determined from the mass separation between the monoisotopic peak of the peptide containing the natural distribution of $^{14}N/^{15}N$ and the monoisotopic peak of the $^{15}N$-enriched counterpart. The data was analyzed using software that was developed in-house to identify the proteins from which the peptides were derived. The software compares the experimentally determined molecular weight and nitrogen stoichiometry with values in a look-up table that is populated with the predicted tryptic fragments (up to 1 missed cleavage) for all protein sequences for the organism in question. A peptide is considered to be identified when there is only one predicted peptide that meets the following match criteria: the predicted peptide has a mass that lies within a specified mass tolerance of the measured molecular weight, and it has the same nitrogen stoichiometry as the measured value. Peptide identifications were made using a mass tolerance of 10 ppm.

Results and Discussion

Figure 2A:
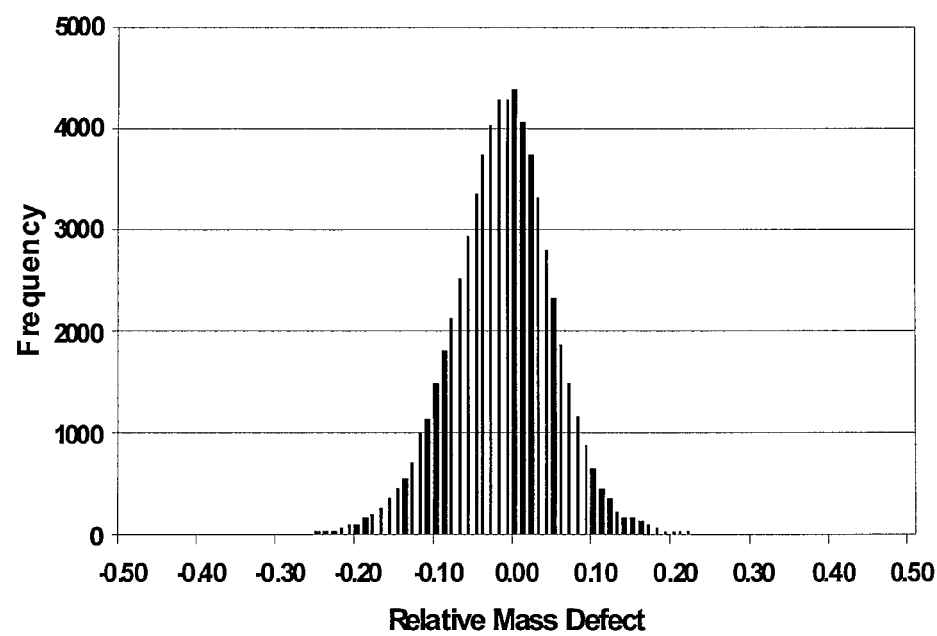
FIG. 2A illustrates the composite distribution of mass defects for all tryptic peptides of M. maripaludis with molecular weights between 700-3500 amu. The horizontal axis is the mass difference (amu) between a peptide's mass defect and the average mass defect for all peptides of the same nominal mass.

Mass Defect Labels: The narrow distribution of mass defects that is characteristic of peptides arises in part from the small mass defect of their component elements, and from the uniform stoichiometry of peptides. Table 1 shows the mass defect of the elements that comprise proteins. As can be seen, their mass defects are small (less than 10 mmu for H, C, N, and O, and around 28 mmu for S). The average elemental ratio for an amino acid residue is $C_{4.9384}H_{7.7583}N_{1.3577}O_{1.4773}S_{0.0417}$. Given that nitrogen (mass defect=+3.1 mmu) and oxygen (mass defect=-5.1 mmu) have comparable stoichiometric values, their mass defects tend to cancel in a peptide. One can see that the mass defect of a peptide is principally due to hydrogen, and that the distribution of mass defects comes from the narrow distribution of elemental stoichiometries. FIG. 1 suggests that the distribution of mass defects at any nominal mass is roughly one third of an amu. One can calculate the distribution of mass defects at each nominal mass for the tryptic peptides of all proteins in a database, and we have done this for peptides with masses from 700-3000 that derive from the proteins in the *M. maripaludis* database. The composite distribution of mass defects around the average value at each nominal mass is shown in FIG. 2A. As can be seen, peptides masses occupy only one-third of the available mass scale, which causes some of the predicted masses to overlap, even at a mass tolerance of 10 ppm. To shift some of the peptide masses to the region of the mass scale that is unpopulated, we alter the mass defects of a portion of the peptides by derivatizing a less frequently occurring amino acid, cysteine, with a reagent that introduces a large mass defect. This is accomplished by introducing a heavy element with a large mass defect into the elemental composition, in this case, bromine.

TABLE 1

Mass difference from nucleon value of the most abundant isotope of the elements found in proteins.

| Element | Mass Defect (amu) |
|---------|-------------------|
| $^{12}C$ | 0 |
| $^{1}H$ | 0.0078 |
| $^{16}O$ | −0.0051 |
| $^{15}N$ | 0.0031 |
| $^{32}S$ | −0.0279 |

Figure 2B:
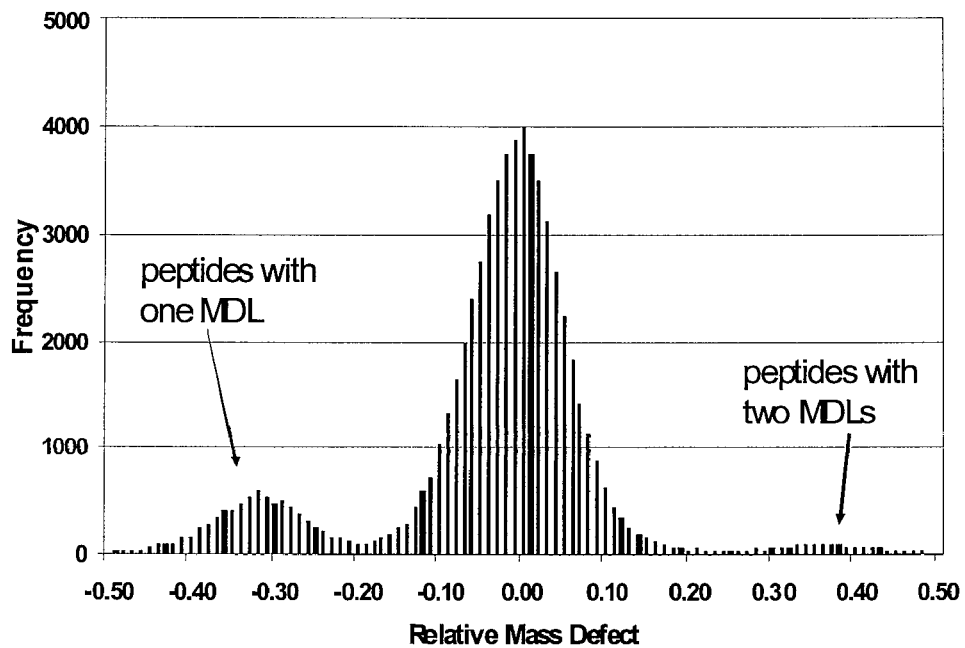
FIG. 2B illustrates the composite distribution when all the cysteine-containing peptides have been labeled. The central distribution corresponds to all peptides that do not contain cysteine. All singly labeled cysteine-containing peptides appear in the smaller distribution centered at −0.30 amu. Doubly labeled cysteine-containing peptides appear at +0.40 amu.

Derivatization of a specific amino acid with a compound that affects the mass defect will yield two sets of peptides; unlabeled peptides with typical mass defects, and labeled peptides with masses that lie in a region of the mass scale that is unoccupied by underivatized peptides. To achieve this end, we have synthesized a reagent that we refer to as a mass defect label (MDL) that derivatizes a specific type of amino acid and that changes the mass of the resulting product in a manner that makes it easy to distinguish derivatized peptides from other peptides of the same nominal mass. The ideal tagging reagent will (1) have high reaction specificity for a low abundance amino acid such as cysteine or tryptophan, (2) introduce a mass defect shift of 0.3-0.6 amu, (3) be stable to the chemical and physical conditions necessary for derivatization and mass spectral characterization, and (4) have no deleterious effects on peptide solubility or ionization efficiency. The MDL reported here is a derivative of iodoacetamide and reacts specifically with cysteine, as shown in FIG. 3. FIG. 2B illustrates the change in the mass defect distribution for the tryptic peptides that is expected from cysteine-derivatization of all the proteins in the *M. maripaludis* sequence database. The derivatized peptide masses occupy a region in which no unlabeled peptides are found, approximately 0.3 amu below the unlabeled peptides. Because only 15-20% of tryptic peptides contain cysteine, fewer peptides will occupy the new region of mass, and therefore there is a lower probability of mass overlap for predicted peptides. This suggests that a higher proportion of derivatized peptides can be identified by their mass compared to underivatized peptides.

Figure 4:
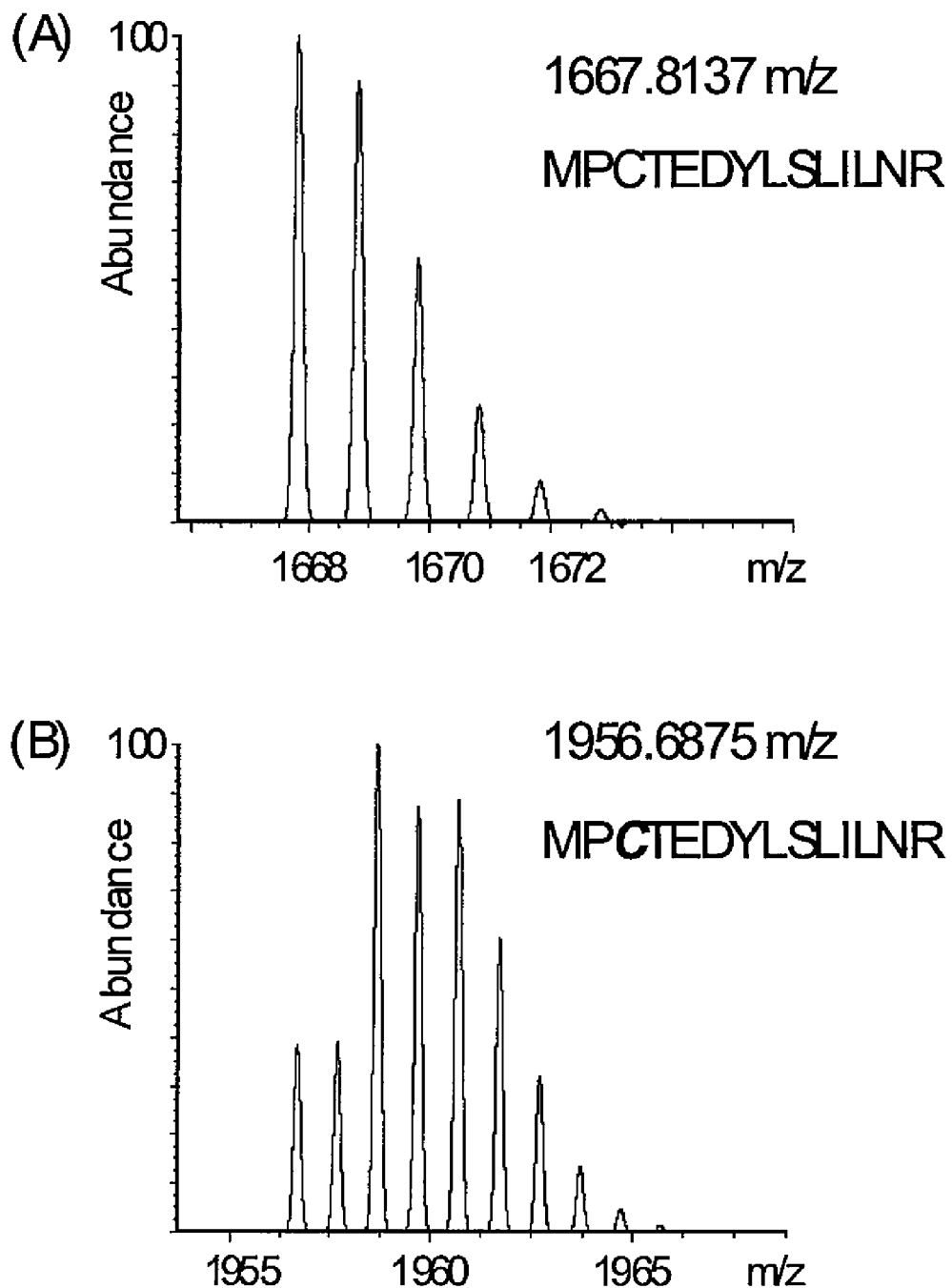

Labeling of Protein Standards: Several protein standards were tested, including bovine serum albumin, β-lactoglobulin, ovalbumin, and carbonic anhydrase. These proteins underwent derivatization of their cysteine residues with the MDL, digestion by trypsin, and analysis by MALDI-FTMS. Mass defect labeled peptides could be identified both by their mass defect values and by the isotope pattern that is characteristic of the presence of two bromine atoms. FIG. 4 shows the calculated isotopic distribution of a peptide (BSA 445-458) that is labeled by the mass defect reagent and compares the distribution to that of the corresponding unlabeled peptide. The use of chlorine isotope patterns to identify derivatized cysteine-containing peptides in a proteomics assay has been reported previously. Here, we do not use the isotopic pattern to establish that derivatization has occurred. The mass defect of the resulting peptide provides this information.

However, it is important that the unusual isotopic pattern is taken into consideration when assigning the monoisotopic peak.

Figure 5:
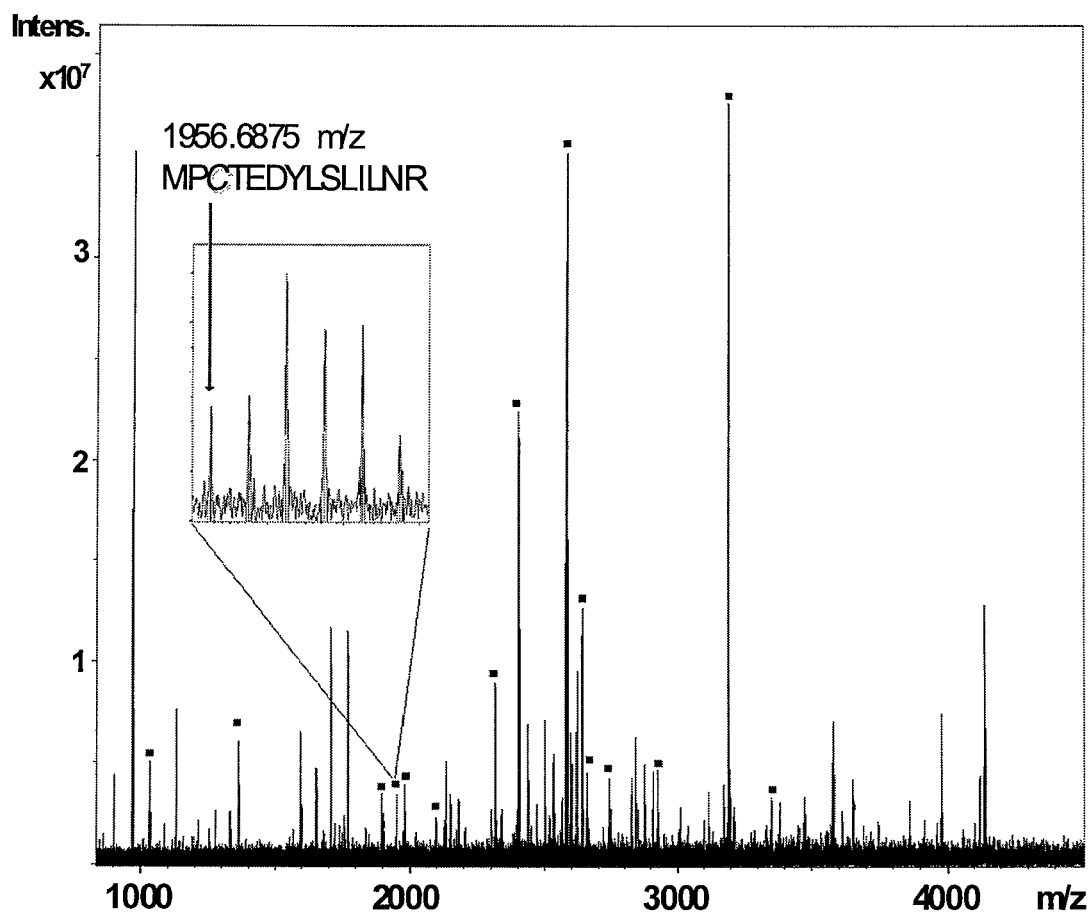
FIG. 5 illustrates the MALDI-FTICR mass spectrum obtained of a bovine serum albumin digest; mass defect labeled-peptides are denoted with a box. Inset shows a mass scale expansion of the peaks near m/z 1957, identified as the peptide MPCTEDYLSLILNR (SEQ ID NO: 1), whose predicted isotope pattern is shown in FIG. 4(B).

FIG. 5 shows a mass spectrum of the tryptic peptides of bovine serum albumin that has been derivatized with the MDL; peaks corresponding to labeled peptides are identified with a square. As can be seen in the mass spectrum, many of the abundant peaks in the mass spectrum are from derivatized peptides, demonstrating that the MDL does not adversely affect the detectability of the peptides. No non-derivatized cysteine-containing peptides were found in the mass spectra for any of the protein tryptic digests that were tested, suggesting that the derivatization reaction was complete. Bovine serum albumin contains 35 cysteines, and 32 labeled cysteine residues were observed in the mass spectra of the tryptic peptides. Interestingly, in the underivatized control spectrum, only five cysteine-containing peptides were observed, suggesting that this derivatization increases the detectability of the cysteine-containing peptides. For β-lactoglobulin, 5 out of 7 possible cysteines were observed in their labeled state, and for ovalbumin, 3 out of 6 labeled cysteines were observed. Bovine carbonic anhydrase II, which does not have a cysteine residue, served as a negative control. No labeled peptides were found in the mass spectrum of its tryptic digest. Overall, these data suggest that the reaction of the MDL reagent is specific for cysteine residues, quantitative in reactivity (no underivatized cysteines was observed), and has no adverse effect on the detectability of the derivatized peptides by MALDI mass spectrometry.

Protein Identification: To test the effectiveness of this method for improving protein identification we derivatized a proteome sample from the organism M. maripaludis. For this experiment, we also use endogenous 15N labeling of protein mixtures to improve the specificity of the protein identification. All proteins from two whole cell lysates are isolated from two identical cultures, one grown using a nitrogen source (ammonium sulfate) with the natural abundance of $^{15}$N and the other with 98% $^{15}$N. Equal amounts of protein are then collected from each culture, and combined. This method is a useful tool to assist with protein identification. Previously, we have found a significant improvement in the ability to identify peptides by accurate mass measurement when nitrogen stoichiometry is used as a search constraint.

M. maripaludis contains 1,722 open reading frames (ORF's), and 18% of the 95,719 predicted tryptic peptides with up to 1 missed cleavage contain cysteine. The utility of this approach ($^{15}$N and MDL labeling) to protein identification by accurate mass measurement has been estimated for this organism at a mass search tolerance of 10 ppm; the fraction of unique peptides increases from 8 percent (unlabeled peptides) to 43 percent (labeled peptides) when all the possible peptides up to m/z 3500 are taken into account. If only the mass defect labeled cysteine-containing peptides are considered, 75% of the masses are unique (database searching with 10 ppm mass tolerance and using the nitrogen stoichiometry as a search constraint).

Increasing the percentage of identified peptides should increase the number of identified proteins. This was examined for the M. maripaludis proteome. Whole cell lysates from M. maripaludis were derivatized and digested by trypsin and subsequently fractionated by nano-LC using a C18 column. The fractions were analyzed by MALDI-FTMS. Analysis of the spectra resulted in the assignment of 1449 non-redundant peptides masses. Out of these, 156 (11%) were found to be mass defect labeled peptides. Using these data, a search was made against a list of predicted M. maripaludis tryptic peptides masses. Using a mass tolerance of 10 ppm, this resulted in the identification of 304 proteins using both nitrogen stoichiometry and mass defect labeling, which is an improvement of 14% over the 268 proteins identified when the search is made against a list that does not include the MDL-peptides. We have previously analyzed the same proteome (but without mass defect labeling or cysteine alkylation) several times under similar conditions, and we typically identify 275±25 proteins. We attribute the improvement in proteome coverage to the fact that mass defect labeling increases both the detectability and the identification specificity of cysteine-containing peptides. To check the effect of the MDL on the detectability of cysteine-containing peptides, we have made MALDI-FTMS measurements of the tryptic digest products of bovine serum albumin (BSA) prepared using three different methods; (1) with no alkylation of cysteine; (2) with alkylation by iodoacetamide (carbamidomethylation); (3) with alkylation by the mass defect label. Each of the three digests were analyzed four times. Of the 35 cysteine residues in BSA, we observe 4-6 (average equals 5) when the cysteines are not alkylated, 8-15 (average 11.3) when cysteines are alkylated by iodoacetamide, and 12-20 (average 15.5) when the mass defect label is used. These data show that the MDL procedure provides 50% better detectability for cysteine-containing peptides compared to carbamidomethylation, and 300% improvement compared to peptides with unalkylated cysteines.

Figure 6:
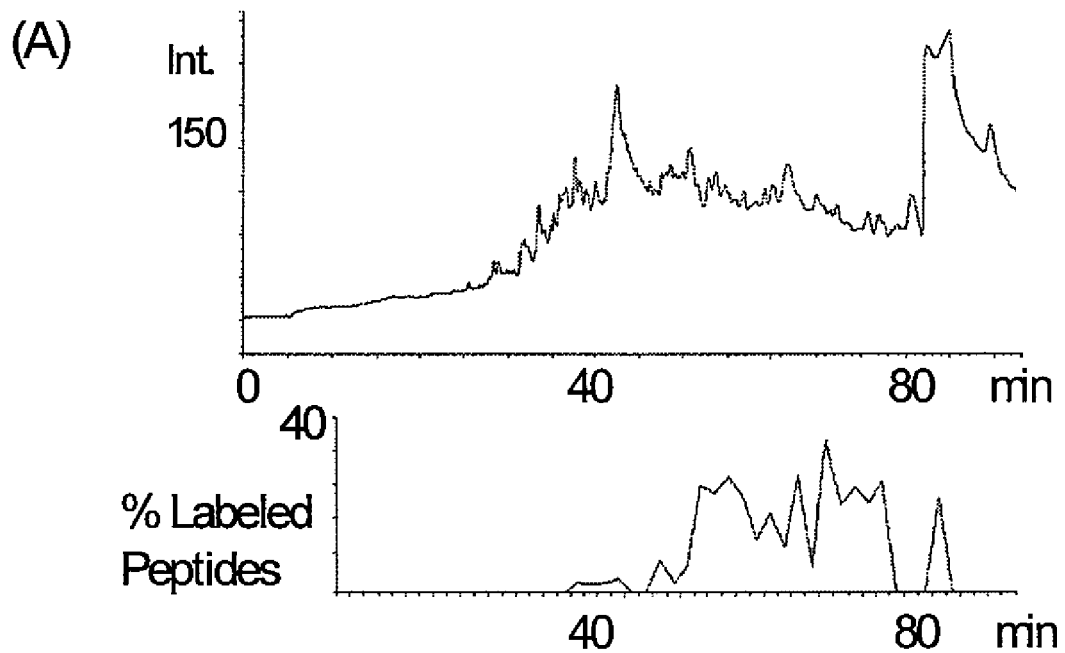
FIG. 6(A) illustrates a chromatogram and plot of percentage of labeled peptides versus elution time for C18 column proteome separation.
FIG. 6(B) illustrates a chromatogram and plot of percentage of labeled peptides versus elution time for C8 column proteome separation. Percent of labeled peptides was calculated using the total number of peptides observed and the number of MDL peptides found for each fraction collected, and analyzed by MALDI-FTICR mass spectrometry.
Figure 6:
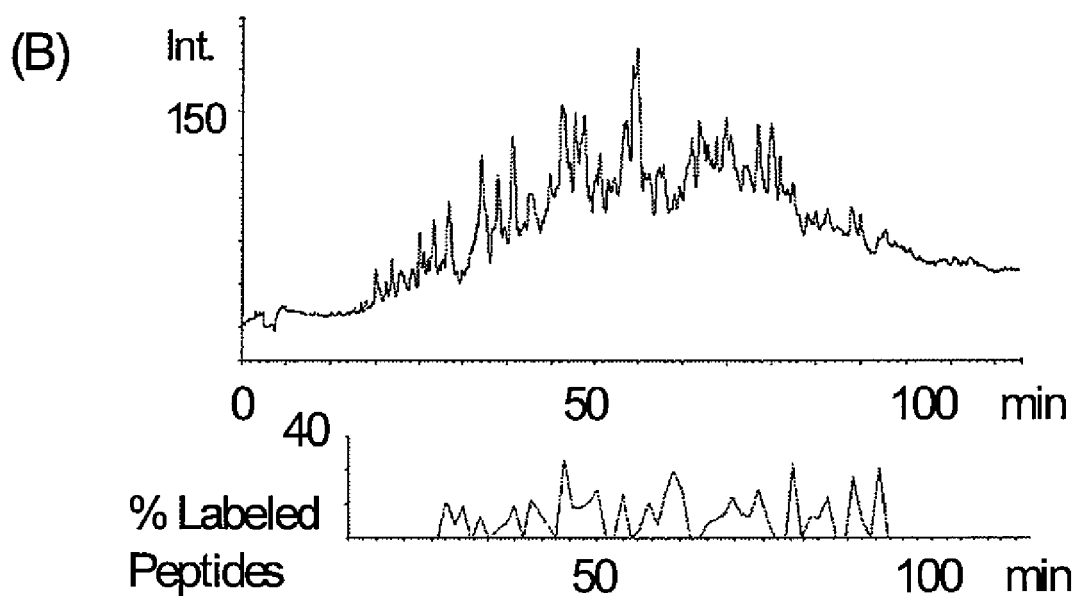

Detailed analysis of the data gave some insight into the hydrophobicity of the labeled peptides. FIG. 6(A) shows a graph of the percentage of labeled peptides found per fraction versus the retention time. Most of the labeled peptides eluted from the column after the gradient reaches 50% organic composition. These data suggest that the labeled cysteine-containing peptides are more hydrophobic, consistent with the structure of the mass-defect label. Earlier elution and better separation of this sample can be achieved by using a column with a less hydrophobic stationary phase. We have examined the same labeled proteome using a C8 column. Analysis of the data resulted in assignment of 1195 pairs of non-redundant peptides masses, of which 126 (11%) were mass defect labeled peptides. FIG. 6(B) shows the percentage of labeled peptides per fraction versus retention time with the C8 column. The labeled peptides are found to be distributed more evenly throughout the LC separation with the C8 column. Nevertheless, the total number of identified proteins shows a slight decrease when compared with the data obtained using a C18 column (279 versus 307 identified proteins). Based on the results obtained it appears that earlier elution of mass defect labeled peptides does not seem to positively affect the total number of those peptides observed by MALDI-FTMS.

Combining both sets of data, the total number of observed peptide pairs ($^{14}$N/$^{15}$N) is 6146; 475 of these were found to be labeled with the cysteine-specific reagent. It is useful to use this large data set to examine the improvement in database searching that results from mass defect labeling and metabolic $^{15}$N labeling. For peptides without a mass defect label, the fraction of unique peptides goes from 7 percent when using only the molecular weight to search the database (i.e., no nitrogen stoichiometry data used in search) to 27 percent for the non-MDL peptides when the nitrogen stoichiometry constraint is used. For the mass defect labeled proteome, the number of unique peptides increases to 2108, which represents 34 percent of the total number of peptides. If one considers only the peptides labeled by 2,4-dibromoacetanilide, 47% of the peptides are identified. Having a higher percentage of unique peptides increases the number of identified proteins. Indeed, identification of proteins shows that if only the non-labeled peptides are used, 377 proteins are identified compared to 425 proteins identified when all the found peptides masses are used. These "extra" 48 proteins are not usually identified from the complex mixture of proteins from *M. maripaludis* by the standard protocol (no cysteine alkylation), demonstrating that better protein coverage is obtained by using the accurately measured masses of mass defect labeled cysteine-containing peptides to identify proteins.

Figure 7:
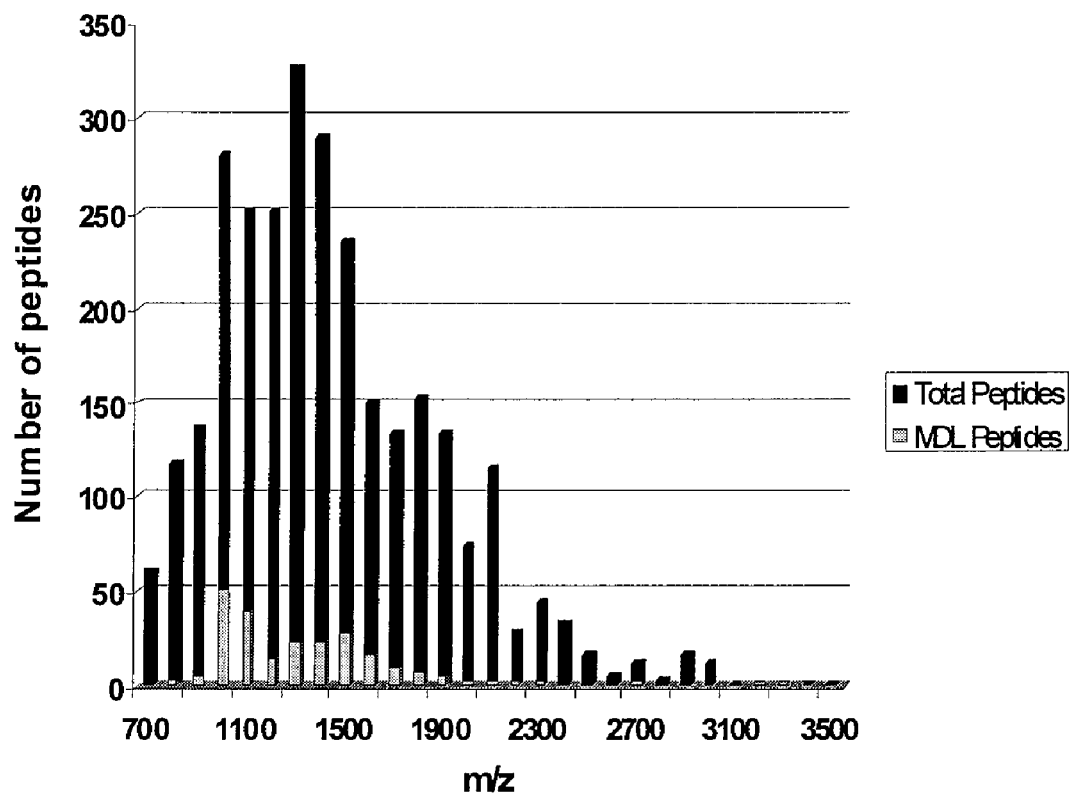
FIG. 7 illustrates a histogram for all possible tryptic peptides from *M. maripaludis* within 700 and 3500 amu. Gray bars represent the number of MDL peptides and black bars the total number of peptides for each 100 amu mass bin.

We anticipate significant improvement in this method by refinement of this technique. For example, we note that the percentage of identified peptides obtained in these experiments is lower than one would predict from a statistical analysis of the proteome. The expected identification specificity mentioned above (43% identification for non-MDL peptides, searching at 10 ppm mass tolerance and using the nitrogen stoichiometry as a constraint; 75% identification for MDL-peptides) was calculated using all the possible tryptic peptides in the mass range of 700-3500 amu. FIG. 7 shows a plot of the number of peptides observed versus their mass-to-charge for the experiment using a C18 analytical column. Most peptides are found in the range between 700 and 2500 amu. The calculated fraction of unique peptides for the tryptic peptides within this mass range is 36% that corresponds well with the observed experimental result of 34%. Detection of higher mass peptides can be achieved by optimizing the operational conditions of the instrument MALDI-FTMS. For the instrument used in these studies, by optimizing the higher mass region of the mass range, the sensitivity of the lower mass region is reduced. Recently, it has been demonstrated in our laboratory that by combining data collected using two different sets of tuning conditions the dynamic range for the analysis of a proteome can be improved. Another approach to increasing the number of mass defect labeled peptides observed is analyzing them by ESI-MS. It has been found in previous studies that ESI is more favorable for the ionization and detection of hydrophobic peptides than is MALDI. Therefore, more mass defect labeled cysteine-containing peptides are expected to be observed by using ESI compared to MALDI.

Conclusions

The method presented here provides a way to improve the specificity of peptide identification based on accurate mass measurement, which leads to an increase in the number of proteins that can be identified in an organism with small genome (<5000 ORF's). This approach has several significant differences from methods that use derivatives with affinity tags, such as ICAT reagents. First, both unlabeled and mass defect labeled peptides are analyzed simultaneously, which eliminates the need for separation prior to analysis and allows the detection of proteins that do not contain cysteine. Second, improvement in specificity arises from the decongestion of the mass spectrum, meaning that regions of the mass space that were previously unoccupied will be populated by the labeled cysteine-containing peptides. Another important advantage of using this approach constitutes the identification of proteins usually missed by other methods; in this case 48 extra proteins were identified by adding a mass defect tag to the cysteine-containing peptides, as this is found to improve both their detectability and their identification specificity. In addition, the analysis of these samples was performed by MALDI-FTMS without requiring the use of tandem MS, which demands the acquisition of much larger data sets, and requires significantly more computational analysis of the data. This approach can be extended to the labeling of other amino acids that occur with lower than average frequency, such as tryptophan, by using labeling reactions that are specific for these amino acids.

Example 2

Accurate mass measurement of proteolytic peptides by FTICR mass spectrometry offers a method for rapidly identifying the components of a proteome sample. We have developed a new method for improving the specificity of protein identification that relies upon derivatizing selected amino acids with compounds that alter their mass defects.

We define mass defect as the difference between the exact mass of a compound and its nominal molecular weight calculated using integer atomic masses. In contrast to small molecules, peptides have significant mass defects due to the numerous atoms present in peptides; however, the distribution of their mass defects is generally narrow, causing peptide masses overlap each other. Peptide assignment would be more specific if the peptide masses are distributed more evenly across the mass scale. This can be achieved by the method "mass defect labeling", in which the masses of the labeled peptides shift to a region of mass scale that is not occupied by unlabeled peptides. In this method, the elements with large mass defect can be incorporated into a tagging reagent to serve as mass defect label (MDL). Bromine is an ideal mass defect element because of its large mass defect (−82.0 mmu).

Figure 8:
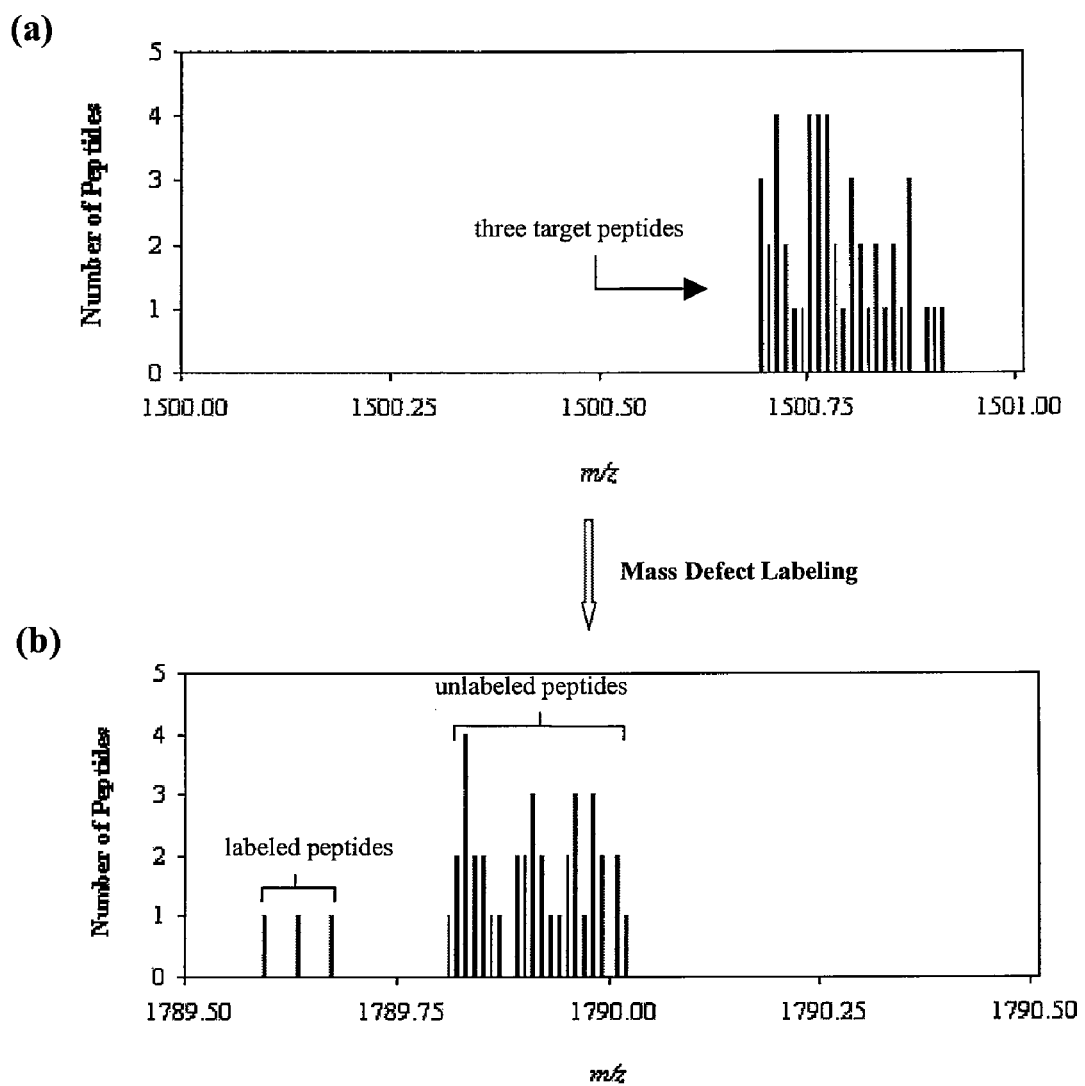

FIG. 8(A) illustrates a histogram of monoisotopic masses for all the possible peptides from in-silico tryptic digestion of *Methanococcus maripaludis* over the range 1500-1501 Da before mass defect labeling, while FIG. 8B illustrates a histogram of monoisotopic masses for all the possible peptides after mass defect labeling.

Methods

Reactions/Procedures:

Phenyl sulfenyl chlorides are known to have high reaction specificity for tryptophan. Nitrophenyl sulfenyl chloride produces a product that is unstable to MALDI analysis (reference our 2006 paper in European Journal of Mass Spectrometry, vol. 12, pp. 213-221.)) The trifluoromethyl derivative is stable in solution and has high reaction specificity for tryptophan. The dibromo-trifluoromethylphenyl sulfenly chloride makes a MDL for tryptophan, and that can be reacted with proteins prior to enzymatic digestion for shotgun proteomic analysis.

Results and Discussion

As noted in Example 1, we have synthesized and demonstrated the efficacy of a MDL for tagging cysteine residues in proteins. In this Example, we describe the development of a MDL with specificity toward tryptophan and test its efficacy with peptide and protein standards.

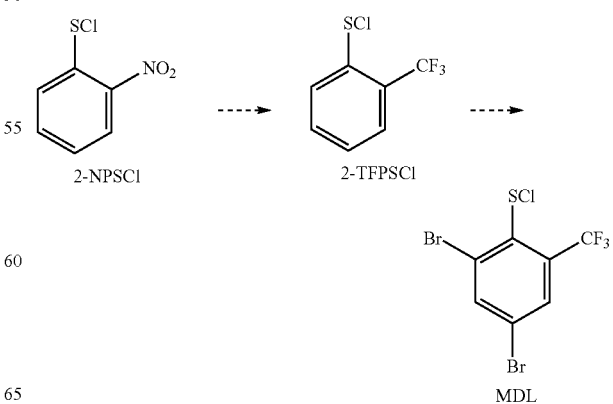

Figure 10:
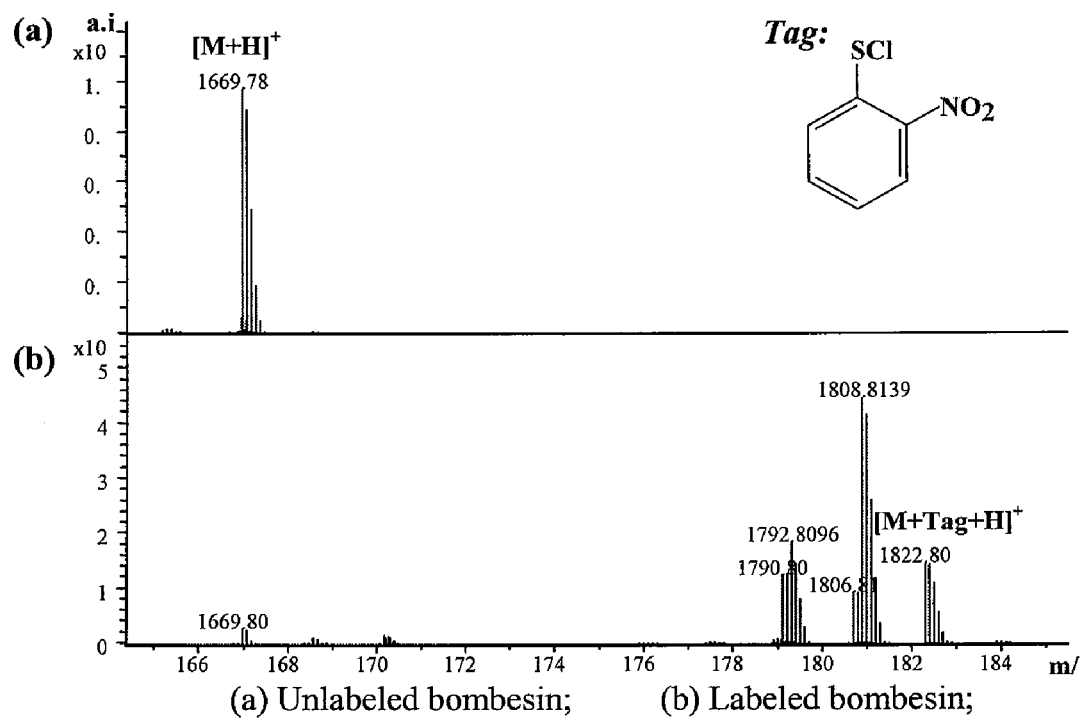
FIGS. 10(a) and 10(b) illustrates the derivatization of bombesin with 2-NPSCI.

Initially, 2-nitrophenylsulfenyl chloride (2-NPSCI) was used as a highly specific reagent for tagging tryptophan residues. We have found that this compound undergoes UV dissociation during MALDI analysis (FIG. 10). FIG. 10 illustrates the derivatization of bombesin with 2-NPSCI.

Figure 11:
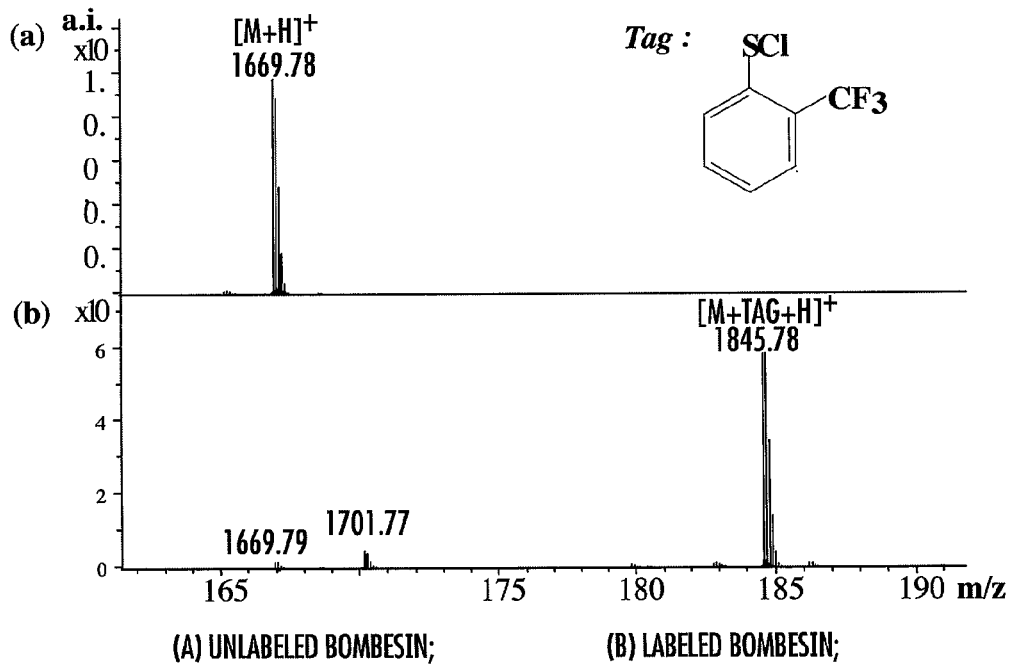
FIGS. 11(a) and 11(b) illustrates the derivatization of bombesin with 2-NPSCI.
Figure 12:
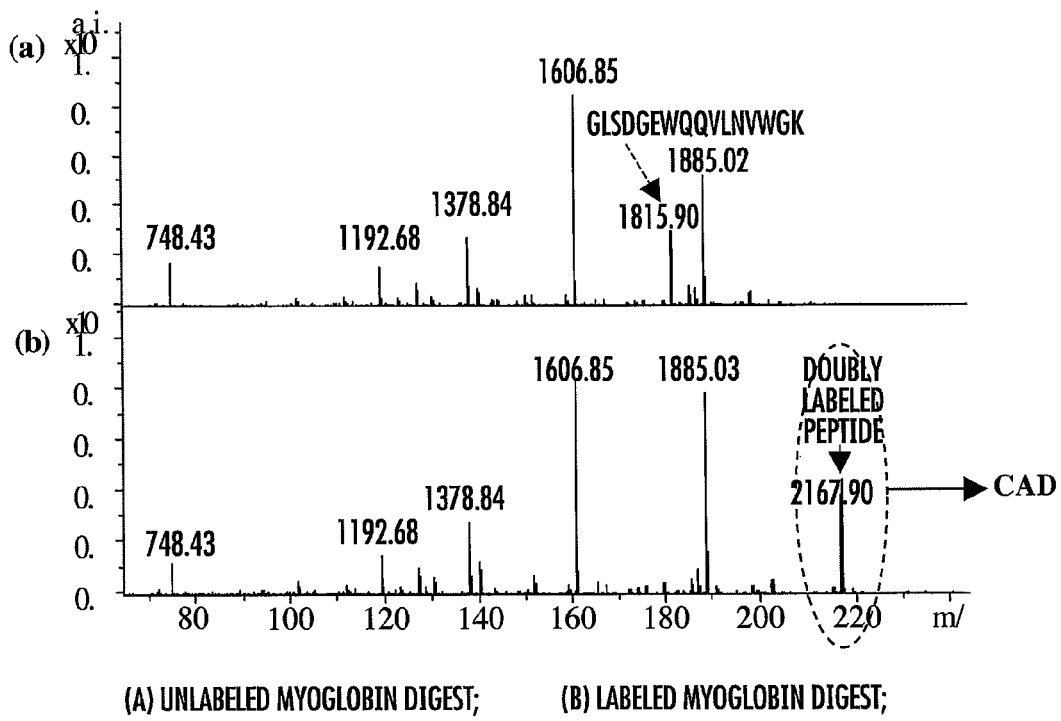
FIGS. 12(a) and 12(b) illustrates the derivatization of myoglobin with 2-TFPSCI
Figure 13:
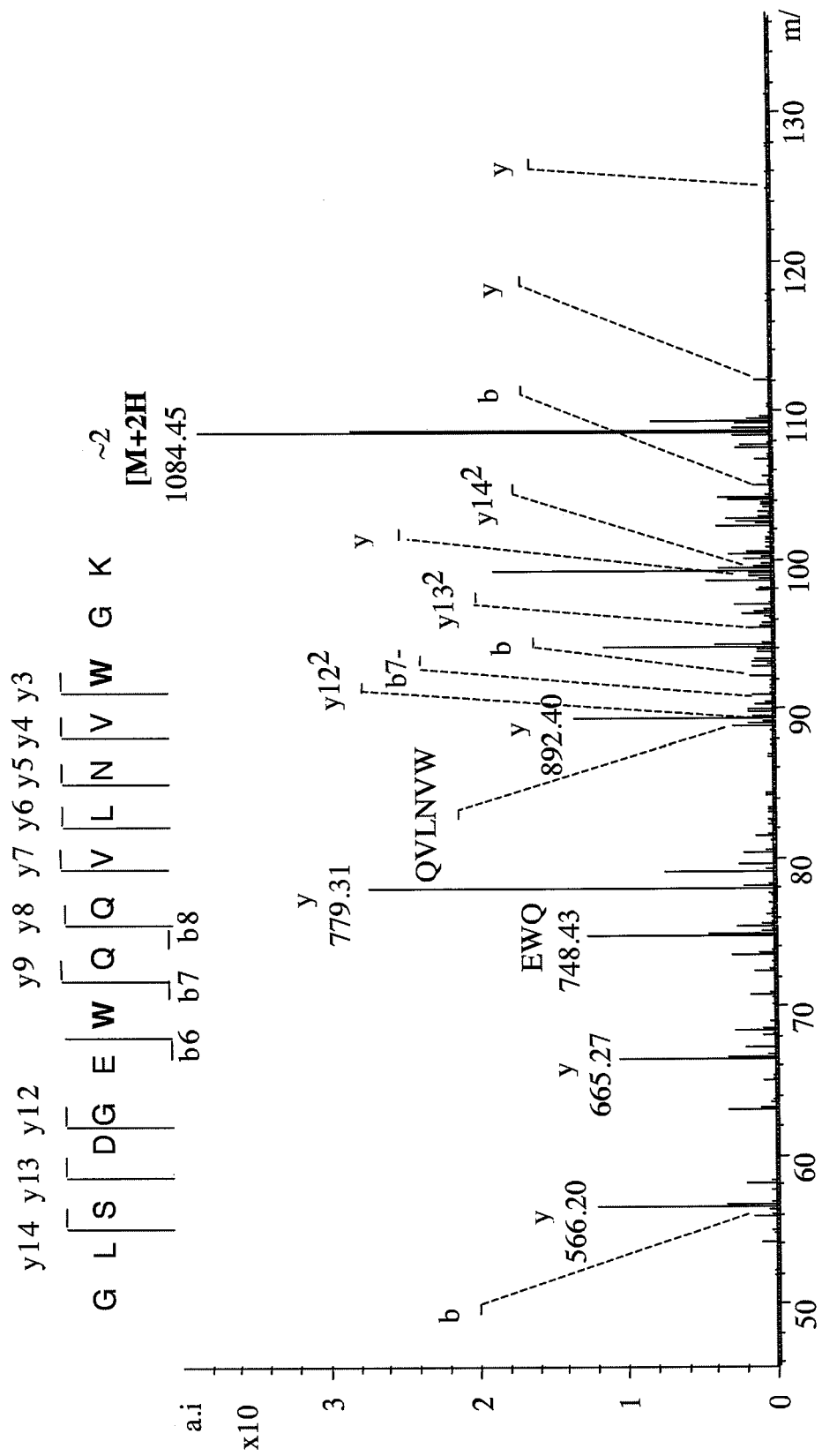
FIG. 13 illustrates the CAD of 2-TFPS-labeled peptide from myoglobin.

To eliminate the photodissociation of 2-NPSCI, we have developed a new tryptophan derivatizing reagent, 2-trifluoromethylphenylsulfenyl chloride (2-TFPSCI), and have tested it with peptide (FIG. 11) and protein (FIG. 12). The labeled peptide in myoglobin was isolated and fragmented by CAD, showing the high specificity of 2-TFPSCI toward tryptophan (FIG. 13). Results show that this tag is stable toward MALDI analysis.

FIG. 11 illustrates the derivatization of bombesin with 2-NPSCI. FIG. 12 illustrates the derivatization of myoglobin with 2-TFPSCI. FIG. 13 illustrates the CAD of 2-TFPS-labeled peptide from myoglobin.

Figure 14:
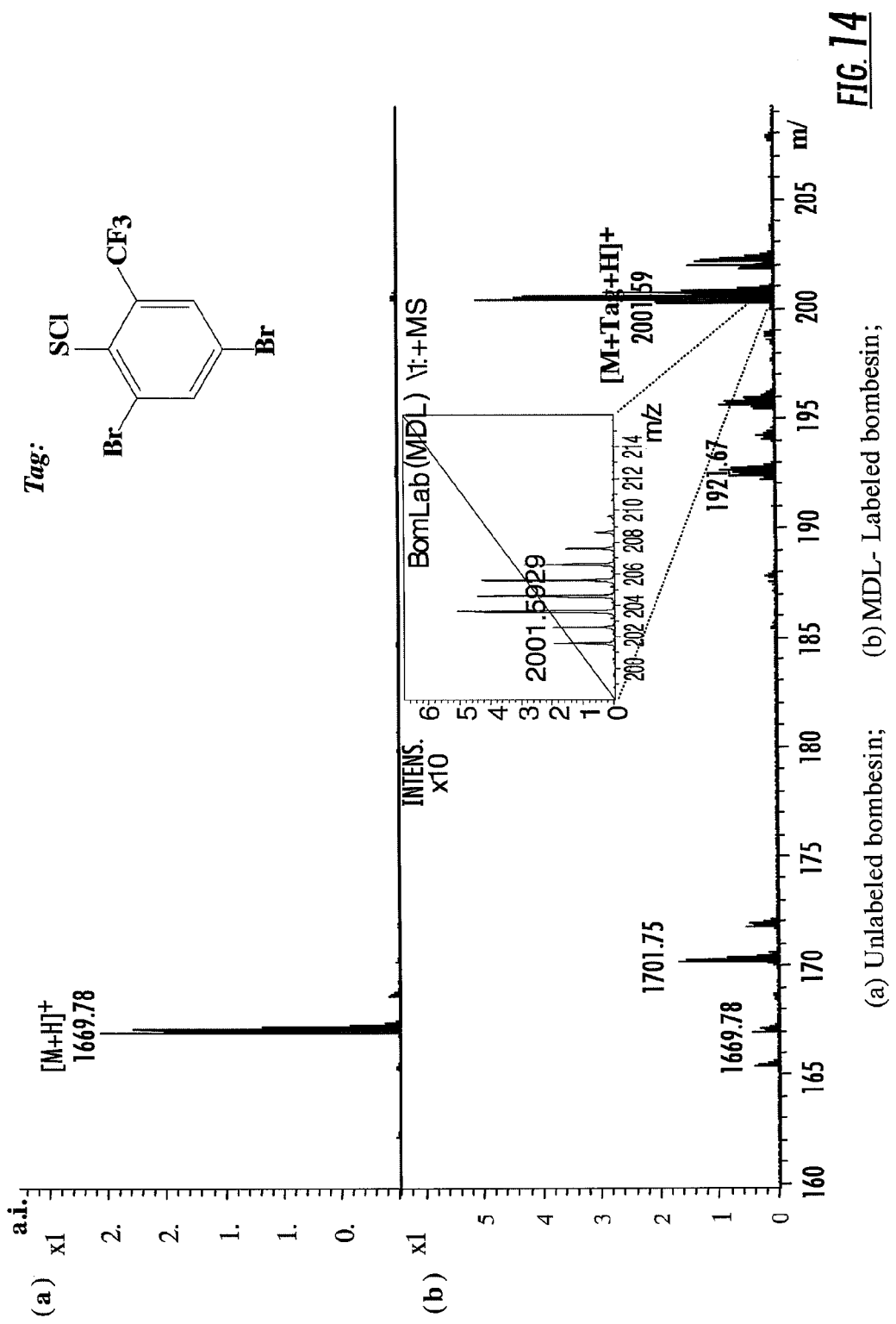
FIGS. 14(a) and 14(b) illustrates the mass defect labeling of bombesin.

To function as a MDL reagent for tryptophan, the dibromo derivative of 2-trifluoromethylphenylsulfenyl chloride has been synthesized. We have tested this MDL reagent with peptide and demonstrated its efficacy for tagging tryptophan residues (FIG. 14). FIG. 14 illustrates the mass defect labeling of bombesin.

Conclusion

2-TFPSCI shows identical reaction specificity and efficiency toward tryptophan compared to 2-NPSCI. 2-TFPSCI exhibits high photostability in MALDI-FTMS analyses. A MDL reagent was developed for tryptophan, and it shows the high reaction specificity toward tryptophan.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A peptide comprising:
   a mass defect labeled peptide including at least one cysteine, wherein at least one of the cysteine residues are labeled with 2,4-dibromo-acetanilide.

2. The peptide of claim 1, wherein the mass defect labeled peptide includes at least one tryptophan, wherein at least one of the tryptophan residues are labeled with 4,6-dibromo-2-trifluoromethylphenylsulfenyl chloride.

3. A method of identifying peptides comprising:
   labeling at least one cysteine in a target peptide with a mass defect label, wherein the mass defect label is 2,4-dibromo-acetanilide;
   introducing the target peptide to a mass spectrometry system; and
   obtaining a mass spectrum of the target peptide.

4. The method of claim 3, further comprising:
   labeling at least one tryptophan in the target peptide with a mass defect label, wherein the mass defect label is 4,6-dibromo-2-trifluoromethylphenylsulfenyl chloride.

5. The method of claim 3, wherein the mass spectrometry system is selected from an ion trap mass analyzer system (IT-MS), an ion cyclotron resonance mass analyzer system (ICR-MS), and an orbitrap system.

6. A peptide comprising:
   a mass defect labeled peptide including at least one tryptophan, wherein at least one of the tryptophan residues are labeled with 4,6-dibromo-2-trifluoromethylphenylsulfenyl chloride.

7. A method of identifying peptides comprising:
   labeling at least one tryptophan in a target peptide with a mass defect label, wherein the mass defect label is 4,6-dibromo-2-trifluoromethylphenylsulfenyl chloride;
   introducing the target peptide to a mass spectrometry system; and
   obtaining a mass spectrum of the target peptide.

8. The method of claim 7, wherein the mass spectrometry system is selected from an ion trap mass analyzer system (IT-MS), an ion cyclotron resonance mass analyzer system (ICR-MS), and an orbitrap system.

* * * * *